United States Patent [19]

Plicchi et al.

[11] Patent Number: 4,576,183

[45] Date of Patent: Mar. 18, 1986

[54] ELECTRONIC CIRCUIT FOR MONITORING RESPIRATORY PARAMETER FOR CONTROLLING OPERATION OF IMPLANTABLE MEDICAL DEVICE

[76] Inventors: Gianni Plicchi, 77/7, Via Mascarella; Giancarlo Canducci, 27, Via Cesare Pavese, both of Bologna, Italy

[21] Appl. No.: 651,354

[22] Filed: Sep. 17, 1984

[30] Foreign Application Priority Data

Sep. 21, 1983 [IT] Italy .............................. 12624 A/83
Jun. 28, 1984 [IT] Italy .............................. 12550 A/84

[51] Int. Cl.$^4$ .............................................. A61B 5/08
[52] U.S. Cl. .............................. 128/723; 128/419 PG
[58] Field of Search ............... 128/419 PG, 716, 723

[56] References Cited

U.S. PATENT DOCUMENTS

| | | | |
|---|---|---|---|
| 3,593,718 | 7/1971 | Krasner et al. | 128/419 PG |
| 4,036,217 | 7/1977 | Ito et al. | 128/723 |
| 4,289,142 | 9/1981 | Kearns | 128/723 |

*Primary Examiner*—William E. Kamm

*Attorney, Agent, or Firm*—Spencer & Frank

[57] ABSTRACT

A low electric energy consumption circuit to detect parameters associated to the patient's respiration, suitable for the realization of implantable devices, such as implantable and physiologic pacemakers, is designed to detect, at the same sample rate of the impedance in a part of the patient's body, the voltage variations V (ΔZL) corresponding to said impedance with both negative and positive variations from the base line. According to a first scheme, these variations V' (ΔZL) are subsequently processed by means that produce a clean $V_{OUT}$ signal, e.g. a squared one, which shows a transition every time that the difference between minimum value and maximum value and maximum value and minimum value of the input signal exceeds a fixed a preferably programmable value. According to a second scheme, said variations V' (ΔZL) are processed by means producing a signal proportional to the variation speed of the body impedance and by means producing a signal Vm (ΔZL) that is the mean value or the average of the values of the input signal and that is proportional to the patient's pulmonary ventilation (l/min).

9 Claims, 5 Drawing Figures

ELECTRONIC CIRCUIT FOR MONITORING RESPIRATORY PARAMETER FOR CONTROLLING OPERATION OF IMPLANTABLE MEDICAL DEVICE

BACKGROUND AND SUMMARY OF THE INVENTION

The invention refers to implantable pacemakers as those described in European application No. EP-A2-0 089 014 (and corresponding copending U.S. application Ser. No. 06/474,241 in the name of the same applicants) wherein the stimulation/inhibition rate of the pacemaker depends, by a programmable algorithm, on the respiratory rate of the patient, detected through the measurement of the impedances of a subcutaneous part of the patient's chest. Said European application No. EP-A2-0 089 014, and its U.S. counterpart, concerns a unit that extracts a clean signal, e.g. a squared one, from the signal coming from the body impedance variation detecting unit. Said clean signal shows a transition every time that the input signal exceeds a fixed and preferably programmable value. In the structural arrangement of the unit, the suggested solution allows to detect the amplitude variations of the input signal only if said variations are positive in comparison with the base line. The same unit is then able to detect only slow variations of the base impedance. Hospital practice has shown that in some cases the variations of the input signal amplitude of said unit can be both positive and negative with regard to the base line. The present invention relates to a new signal extracting unit for pacemakers, of the type above mentioned, capable to meet said needs and to produce a clean output signal, e.g. a squared one, that shows a transition every time that the difference between a minimum value and a maximum value or a maximum value and a minimum value of the input signal exceeds a fixed and preferably programmable value. Moreover the unit according to the invention is able to perform both slow and fast and recurrent variations of the base line. In consideration of the fact that such a signal extracting unit has proved to be very useful and reliable, the invention proposes further an alternative structural arrangement of the same unit to make it suitable to be assembled in physiologic pacemakers as those described in the Italian patent application No. 12421 A/84 of Feb. 7, 1984 by the same applicants, and corresponding copending U.S. application Ser. No. 06/659,542, wherein the stimulation/inhibition rate depends, by a special programmable algorithm, on the patient's pulmonary minute ventilation (1/min).

BRIEF DESCRIPTION OF THE DRAWINGS

The features of the circuit of said unit and its advantage are apparent in the following description of some preferred embodiments of same, shown by way of non-limiting example in the attached drawings, in which.

DESCRIPTION OF THE PREFERRED EMBODIMENT

Figure 1:
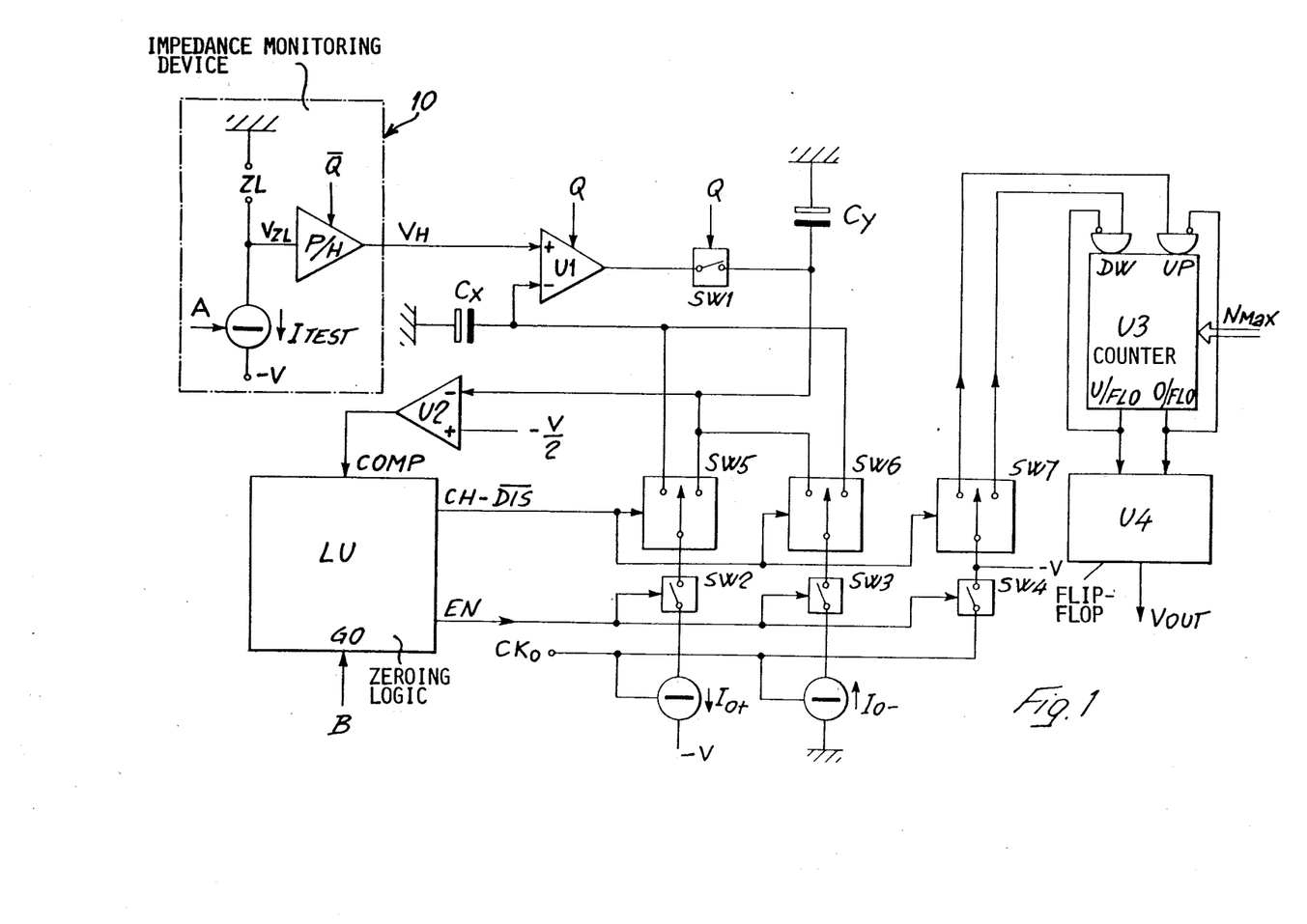
FIG. 1 shows the circuit of the unit processing the output voltage variations of the analyzer and convertor circuit which calculates the impedance variations of a part of the patient's body with a sample rate such as to allow to detect the respiration as described in the mentioned U.S. application Ser. No. 06/474,241.

With reference firstly to FIG. 1, 10 is the reference numeral for the unit already described in application Ser. No. 06/474,241 which detects the impedance variations ZL of the patient's body by producing sample pulses $I_{Test}$ lasting 122 $\mu$s and with a repetition period $T_O = 125$ ms (timing A in FIG. 2). The peak value of the voltage $V_{ZL} = I_{Test} \cdot ZL$ is stored for 366 $\mu$s by a fast "Peak and Hold" (P/H). Said P/H can be avoided if the differential gain (U1) at the unit input according to the present invention (as described hereafter) is sufficiently fast.

In the present scheme in order to save energy, a slow differential amplifier is used in combination with a fast and low consumption P/H. The stay time of the peak voltage (366 $\mu$s) at the P/H output is controlled by the timing Q of FIG. 2 with the same rate as signal A.

Figure 2:
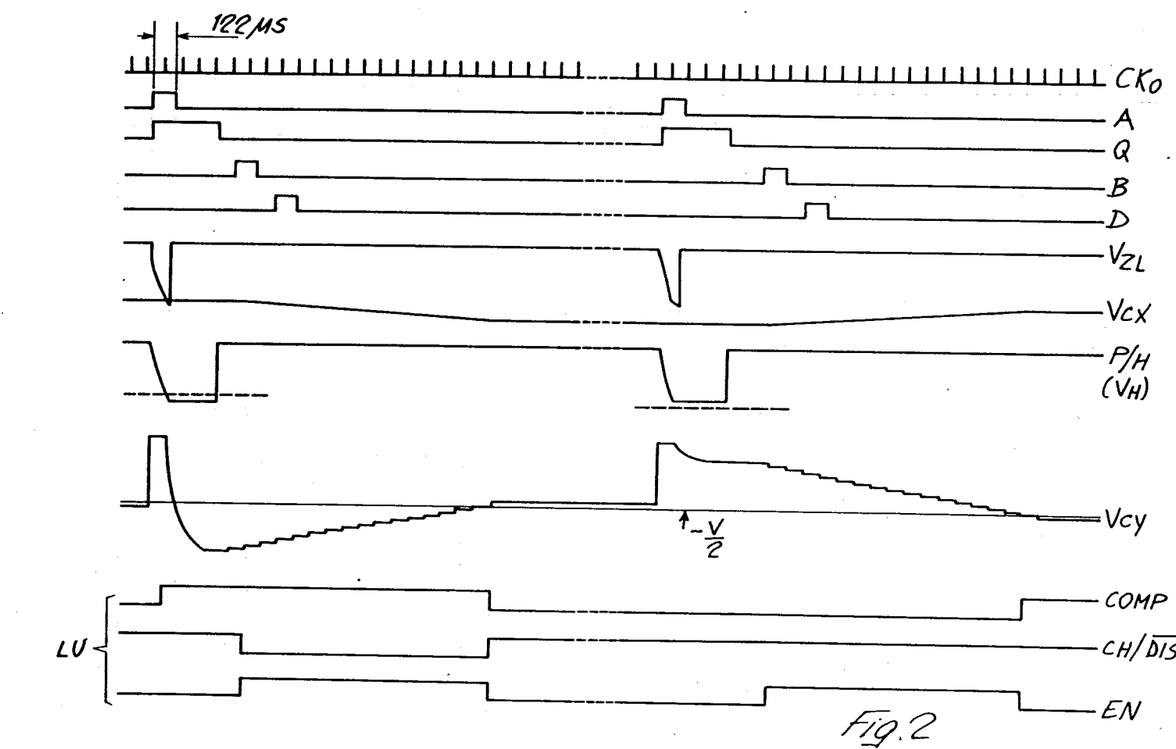
FIGS. 2 and 3 show the features of the circuit signals which are present in the circuit according to FIG. 1.

V/H is the P/H output voltage controlled, as said, by Q shown in FIG. 2. The voltage $V_H$ is applied to the noninverting input of amplifier U1 and when Q is high, via the differential amplifier U1 with gain $A_O$ and switch SW1, closed when Q is high, it determines the charge of condenser Cy. Differential amplifier U1 is fully supplied with operating voltage only when Q is high in order to save energy. Q has the same rate and timing of the sampling. Let us take a general sample cycle called "m". At the end of "m" time interval of 366 $\mu$s, during which Q remained high, Cy is charged with U1 output voltage. The inverting input of amplifier U1 receives the charge voltage of a condenser Cy.

$$V_{Cym} = A_O(V_{Hm} - V_{Cxm}) = -\frac{V}{2} + \Delta V_{Cym} \quad (1)$$

where $-V/2$ is a voltage fixed for the purposes given as a reference and $\Delta V_{Cym}$ the difference, positive or negative, from said reference. It has to be taken into account that all increases $\Delta$ can be either positive or negative.

When Q goes back to low, switch SW1 is opened, therefore Cy is disconnected and charged with $V_{Cym}$.

Figure 3:
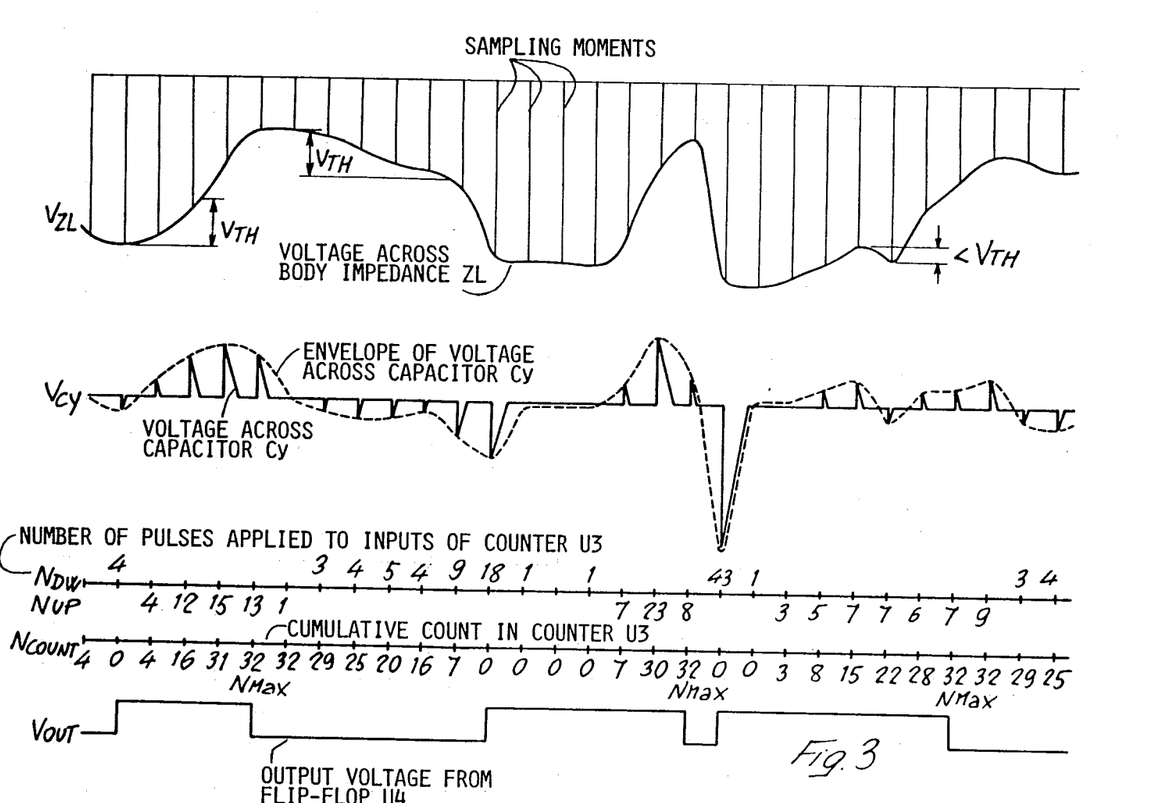

Let's now consider the zeroing logic group LU. There is no detailed description of said group as it can be easily realized by any expert in the field according to the description of the functions given hereafter, taking into consideration the diagram of the timings of FIGS. 2 and 3. LU has two inputs: COMP indicates one of them wherein a comparator U2 compares $V_{Cym}$ and $-V/2$; GO indicates the other one wherein timing B has the same rate of Q but slightly delayed. LU has two outputs: one is called EN and when it is high it closes switches SW2, SW3, SW4, the other, CH/$\overline{DIS}$ commutes switches SW5, SW6, SW7 to the left when it is low and to the right when it is high. EN output goes high with B rising edge and it stays there until there is a change in the comparator output. CH/$\overline{DIS}$ output is low when COMP input is high and high when COMP input is low. After a Cy charge increase and the opening of SW1 for the continuous action of comparator U2, switches SW5, SW6, SW7 are positioned to the right or to the left according to COMP input level that is according to $\Delta V_{Cy}$ sign with reference to $-V/2$. With the arrival of B timing pulse, its rising front triggers off LU which, in its turn, closes SW2, SW3, SW4 allowing as a first consequence, the voltage pulses produced by $I_{O+}$ or $I_{O-}$, lasting $\tau O = 3$ μs, with $I_O$ amplitude and timed by $CK_o$ (FIG. 2) to charge or discharge condenser Cy to cancel $\Delta V_{Cym}$. The canceling takes place after $N_m$ pulses being $$N_m = \frac{C_y}{I_o \cdot \tau_O} \Delta V_{Cym} \quad (2)$$

and, at this point, the discharge is blocked as the sign of Cy voltage changes with regard to $-V/2$ reference voltage on comparator U2, the output of which operates on the logic group LU. During Cy charge adjustment, current pulses with the same amplitude, duration and recurrence rate as those which adjusted Cy, but produced by another $I_{O+}$ and $I_{O-}$ source connected to Cx, modify in the opposite way the charge of Cx that during the "m" cycle increases its voltage $$\Delta V_{Cxm} = \frac{I_o \tau_O}{C_x} N_m = \frac{C_y}{C_x} \Delta V_{Cym} \quad (3)$$

At the end of "m" cycle and at the beginning of "m+1" cycle, Cx voltage becomes:

$$V_{Cx}(m+1) = V_{Cxm} + \frac{C_y}{C_x} \Delta V_{Cym} \quad (4)$$

According to (1), in "m+1" cycle the situation will be:

$$A_O[V_H(m+1) - V_{Cx}(m+1)] = -\frac{V}{2} + \Delta V_{Cy}(m+1) \quad (5)$$

In "m" cycle, $V_H$ voltage increases that is:

$$V_H(m+1) = V_{Hm} + \Delta V_{Hm} \quad (6)$$

and by replacing in (5) the data given by (6) and (4)

$$A_O(V_{Hm} - V_{Cxm}) + A_O \Delta V_{Hm} - A_O \frac{C_y}{C_x} \Delta V_{Cym} = -\frac{V}{2} + \Delta V_{Cy}(m+1)$$

Going back to (1), simplifying and gathering the data we obtain:

$$\Delta V_{Cym}\left(1 - A_O \frac{C_y}{C_x}\right) + A_O \Delta V_{Hm} = \Delta V_{Cy}(m+1) \quad (7)$$

If the capacity and the gain values of the differential amplifier U1 are such that:

$$A_O = \frac{C_x}{C_y} \text{ we obtain:} \quad (8)$$

$$\Delta V_{Cy}(m+1) = A_O \Delta V_{Hm} \quad (9)$$

When (8) is verified Cy voltage referred to $-V/2$ is equal to the gained difference between the present and the previous $V_{ZL}$ sample. If we consider (2), $N_m$ is proportional to said $\Delta V_{Hm}$ difference or, as $T_o$ is constant, to the incremental ratio $(\Delta V_{Hm})/T_o$.

Going back to group LU, it is now clearer that, according to the output state of comparator U2 and, therefore, to $V_{Cy}$ value vis-a-vis $-V/2$, SW5 and SW6 are positioned so as to supply a current with the sign suitable to bring $V_{Cy}$ back to a value close to $-V/2$.

The rising edge of B triggers off $V_{Cy}$ adjustment action by adding or subtracting $I_O \tau_O$ charge quantities in Cy as the same edge closes, through EN output, switches SW2, SW3, SW4 that will reopen when comparator U2 shows the sign change of the difference $V_{Cy} - (-V/2) = \Delta V_{Cy}$.

The action of the first two switches is evident. SW4, according to the position of SW7 that depends, all things considered, on the sign of the incremental ratio, instructs $N_m$ pulses of $CK_o$ to increase ($N_{UP}$) or decrease ($N_{DW}$) a UP/DW programmable and saturating register of finite length indicated with U3 in FIG. 1. By UP/DW saturating register, we mean a register counting in the two directions which stops when it reaches one of the two count limits ($N_{max}$ or O) without accepting further pulses.

In order to make clear what said so far, and in particular function of register U3 and the circuits connected to it, we take an example shown in FIG. 3. We can see the behaviour of $V_{ZL}$ with its samples. Corresponding to it, just below, we see the behaviour of $V_{Cy}$ referred to $-V/2$. If we consider equation (9) and the following considerations we notice that the envelope of $V_{Cy}$ diagram represents the approximate derivative, at a distance of a sample interval of ZL.

Each $V_{Cy}$ sample with positive $V_{Cy}$ (or negative) is associated with a $N_{UP}$ (or $N_{DW}$) which determines its size. These numbers are added algebraically in the register, starting from a saturation state until the next one. The result corresponding to each sample is $N_{COUNT}$ which, once it has reached a higher or lower saturation, it stays there until subsequent subtrahends or addends bring it back within the range with O and $N_{max}$ as limits (programmed from the outside as shown in FIG. 1). In the example of FIG. 3 $N_{max}$ is 32.

The indication of upper (OVERFLOW) or lower (UNDERFLOW) saturation by register U3 are given to a flip-flop U4 that, through the above described process, produces an output signal $V_{OUT}$, depending on $V_{ZL}$. Signal $V_{OUT}$ is high when $N_{COUNT}$ reaches O and low when $N_{COUNT}$ reaches $N_{max}$ value. FIG. 3 shows the relation between the behaviour of $V_{ZL}$ and that of $V_{OUT}$ pointing out the changes in state of the latter one. $V_{OUT}$ depends, as said, on the number of pulses necessary for Cy discharge. The conclusion we draw from FIG. 3 is the following. For each increase of $V_{ZL}$ greater than a given $V_{TH}$ value, starting from its maximum value, there is a negative transition of $V_{OUT}$. $V_{OUT}$ transitions, as already said, take place at the same time of the sample, after exceeding $V_{TH}$ value. The threshold voltage is:

$$V_{TH} = \frac{N_{max} \cdot I_o \cdot \tau_O}{C_x} \quad (10)$$

Although ZL is a particular impedance, for the purposes of the present invention it can be defined as a threshold impedance, considering that $V_{ZL}$ peak $= (-ZL \cdot I_{TEST})$ peak:

$$Z_{TH} = \frac{I_o \tau_O}{I_{TEST} C_x} N_{max} \quad (11)$$

This threshold can be regulated by $N_{max}$ which is programmable from outside.

Taking into account the above algorithm, the operation of the device can be thus summarized. There is a $V_{OUT}$ transition each time that the difference between a minimum (or maximum) impedance value and a maximum (or minimum) value of the following sample exceeds $Z_{TH}$ fixed value. Cases wherein the difference between a minimum (or maximum) value and a maximum (or minimum) value of the subsequent samples are lower than $Z_{TH}$ value are entirely neglected. This statement solves the case of spurious signals (such as those due to the heart beat) overlapping the main signal. In the specific case of application to the transthoracic impedance measurement, the device exclusively detects the relatively large and repeated variations depending on respiration.

Figure 4:
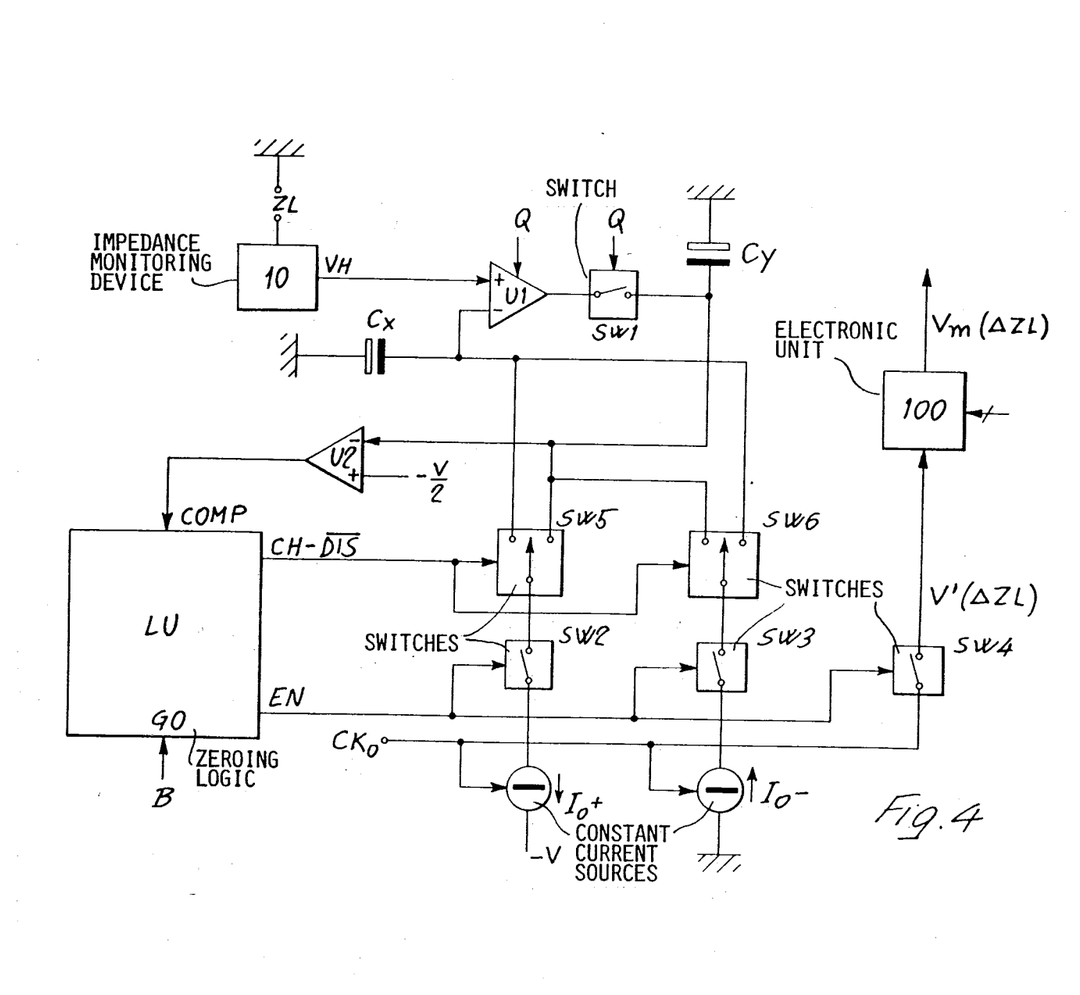
FIG. 4 shows the circuit of FIG. 1 modified in order to use the physiologic pacemaker according to Italian patent application No. 12421 A/84 depending on the patient's pulmonary ventilation.
Figure 5:
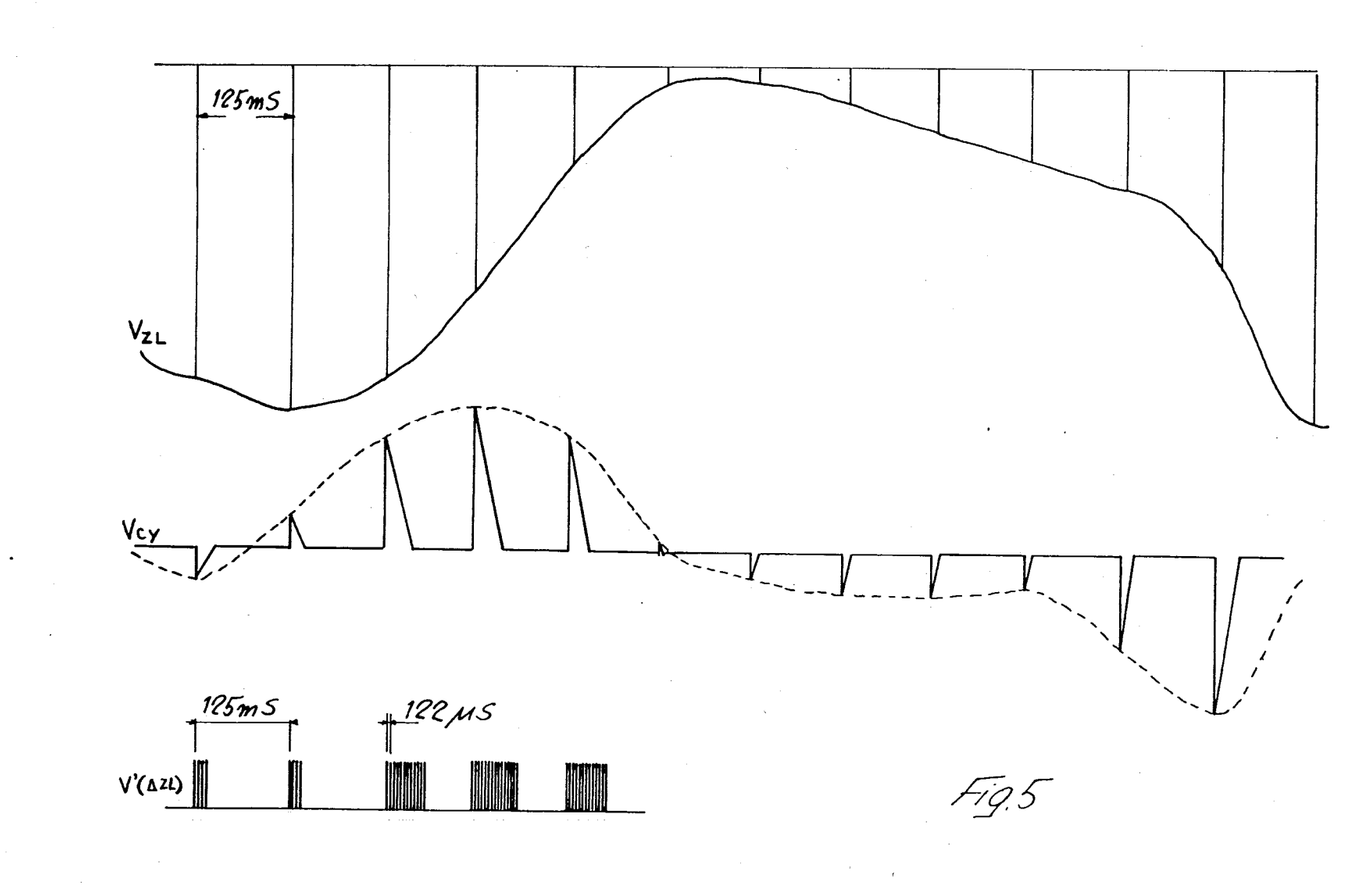
FIG. 5 shows the features of some of the signals present in the circuit in FIG. 4.

In order to be used in the physiologic pacemaker described in Italiam patent application No. 12421 A/84 mentioned in the introduction, wherein the stimulation-/inhibition rate of the pacemaker is controlled by the patient's pulmonary minute ventilation (1/min), the circuit of FIG. 1 can be modified as shown, as an example, in FIG. 4, wherein components SW7 and U3-U4 have been eliminated and at every 125 ms sample interval, pulse trains come out of switch SW4, their quantity being proportional to the body impedance variations between consecutive samples. FIG. 5 shows the behaviour of $V_{ZL}$ with the relevant samples. Corresponding to it, just below, we can see the behaviour of $V_{Cy}$ referred to $-V/2$. Further below, the timing of V' ($\Delta$ ZL) is indicated for the first five samples ($N_{DW}$ and $N_{UP}$ timing of FIG. 3). Signal V' ($\Delta$ ZL) coming out of switch SW4 is sent to an electronic unit 100, for example a microprocessor or other type with low energy consumption and which can be miniaturized, unit which knowing the repetition period (125 ms) of the input pulse trains and the rate (122 $\mu$s) of the same train pulses, produces a signal Vm ($\Delta$ ZL) that is the average of the variation speed of signal V' ($\Delta$ ZL) and is proportional to the patient's pulmonary minute ventilation (1/min).

Signal $V_{OUT}$ in the circuit of FIG. 1 and signal Vm ($\Delta$ ZL) in the circuit of FIG. 4, is sent to a programmable correlator, not shown in the Figures, which produces a pacemaker stimulation/inhibition rate that is proportional to the features of the input signal and suitable for the physiologic demand of the patient.

It is understood that the circuit of FIGS. 1 and 4 can be used in implantable and/or portable devices other than the pacemakers, such as devices physiologically driving the operation of an artificial organ, for example an artificial heart, or in therapeutic and/or diagnostic devices. Lastly, it is understood that the description is referred to a preferred embodiment of the invention, which may be changed or modified, in its constructive realization, without departing form the inventive principle above described and hereafter claimed.

We claim:

1. An electronic circuit for detecting a respiratory parameter in a device which is implantable in a patient's body and which is operable in response to such respiratory parameter, said circuit comprising: a measurement and impedance/voltage conversion unit for detecting the impedance of a part of the patient's body where the impedance varies in dependence on respiration, said unit including sampling means which effects sampling of the impedance during discrete sampling times occurring at selected time intervals, and means for producing an output signal representative of the sampled impedance values; signal processing circuit means connected to said unit for producing, in response to the output signal from said unit, a clean, regular signal representative of deviations of the impedance from a selected base impedance value, said signal processing circuit means comprising signal processing means operable for causing the clean, regular signal to vary between two selected amplitude values each time that, and only when, the difference between successive peak values of the output signal exceeds a selected value; and means for deriving from the clean, regular signal a control signal for controlling the operation of the implantable device.

2. A circuit as defined in claim 1 wherein the sampling time each have a duration of about 122 $\mu$s and the selected time intervals have a period of about 125 ms.

3. A circuit as defined in claim 1 wherein said signal processing circuit means further comprise:
a first capacitor having a grounded plate and an ungrounded plate, and between which plates there is provided a first reference signal;
a differential amplifier connected to receive said output signal from said unit and said first reference signal for producing a first comparison signal representative of the difference between said output signal and said first reference signal;
a second capacitor having a grounded plate and an ungrounded plate;
a first switch connected between said first differential amplifier and said ungrounded plate of said second capacitor for periodically supplying said first comparison signal to said second capacitor in time coincidence with the discrete sampling times associated with said sampling means, for periodically charging said second capacitor to establish at said ungrounded plate of said second capacitor a comparison signal voltage corresponding to said first comparison signal;
a comparator having a first input connected to receive said comparison signal voltage, a second input connected to receive a constant reference voltage, and an output for providing a comparator output signal having a polarity representative of the polarity of said comparison signal voltage relative to said constant reference voltage;
first and second signal controlled electronic devices each having an input, first and second outputs and signal controllable means for conductively connecting said input to a selected one of said first and second outputs;
means conductively connecting said ungrounded plate of said first capacitor to said first output of said first device and to said second output of said second device, and conductively connecting said ungrounded plate of said second capacitor to said second output of said first device and to said first output of said second device;
first and second current sources supplying currents of respectively opposite polarities, each said current source supplying a sequence of constant amplitude current pulses at a constant rate which is higher than the rate of occurrence of the discrete sampling times associated with said sampling means;
second and third switches each of which is connected between a respective one of said constant current sources and said input of a respective one of said electronic devices, and each of which is electronically controllable for selectively conductively connecting together said respective source and electronic device;

logic circuit means having a main input, a start input, first and second outputs and means logically linking said outputs to said outputs to said inputs, said main input of said logic circuit means being connected to said comparator output, said start input of said logic circuit means being connected to receive a periodic timing signal having the same period as, but offset in time from, the discrete sampling times associated with said sampling means, said first output of said logic circuit means being connected for electronically controlling said second and third switches, said second output of said logic circuit means being connected to said signal controllable means of said first and second electronic devices for supplying a control signal thereto, and said means logically linking said outputs to said inputs being operable for:

supplying to said first output of said logic circuit means a signal for causing each of said second and third switches to a selectively conductively connect together its said respective source and electronic device in response to each appearance of the periodic timing signal at said start input; and supplying to said second output of said logic circuit means a signal which is a function of the signals at said main and start inputs for controlling said devices in a manner to vary the charge on said second capacitor, after each occurrence of the periodic timing signal, to bring the value of the voltage at said ungrounded plate of said second capacitor to the value of the constant reference voltage, and to simultaneously vary the charge on said first capacitor in a manner to cause the voltage at said ungrounded plate of said capacitor to change in a direction opposite to the direction of change of the voltage at said ungrounded plate of said second capacitor; whereby the voltage established at said ungrounded plate of said second capacitor during each discrete sampling time is proportional to the difference between the value of said output signal at that discrete sampling time and the value of said output signal at the immediately preceding discrete sampling time.

4. A circuit as defined in claim 3 wherein said signal processing circuit means further comprise:

a fourth switch having an input connected to receive pulses of a clock signal at said constant rate which is higher than the rate of occurrence of the discrete sampling times associated with said sampling means, said fourth switch having an output and electronically controllable means operable for selectively conductively connecting its said input to its said output, said electronically controllable means of said fourth switch being connected to said first output of said logic circuit means for conductively connecting together said input and output of said fourth switch in response ot each appearance of the periodic timing signal at said start input of said logic circuit means and for subsequently disconnecting said input and output of said fourth switch when the value of the voltage at said ungrounded plate of said second capacitor becomes substantially equal to the value of the constant reference voltage; and a third signal controlled electronic device having an input connected to said output of said fourth switch, first and second outputs and signal controllable means connected to said second output of said logic circuit means for selectively conductively connecting said input of said third device to said first output of said third device during each period that said first and second devices are being controlled to vary the charge on said second capacitor in a first direction and for conductively connecting said input of said third device to said second input of said third device during each period that said first and second devices are being controlled to vary the charge on said second capacitor in a second direction which is opposite to the first direction; and wherein said signal processing means comprise: a saturating up-down counter of finite capacity having an up-counting input connected to said first output of said third device, a down-counting input connected to said second output of said third device; means for counting up pulses applied to said up-counting input to a preselected maximum count value and for counting down pulses applied to said down-counting input to a preselected minimum count value, and output means for providing a first output signal each time said means for counting reaches said preselected maximum count value and for providing a second output signal each time said means for counting reaches said predetermined minimum count value; and circuit means for producing a square wave signal which assumes a first value in response to each occurrence of the first output signal and which assumes a second value in response to each occurrence of the second output signal.

5. A circuit as defined in claim 4 wherein the difference between the minimum and maximum count values is 32.

6. A circuit as defined in claim 3 wherein said means for producing an output signal in said measurement and impedance/voltage conversion unit comprises a peak-and-hold circuit having a short hold period for storing, during each hold period, a voltage representing the impedance value sampled during a respective sampling time.

7. A circuit as defined in claim 3 wherein said differential amplifier is supplied with operating power only during the times when said first switch is supplying said first comparison signal to said second capacitor for minimizing power consumption.

8. A circuit as defined in claim 3 wherein each current pulse supplied by each of said current sources has a duration of approximately 30 $\mu$s.

9. An electronic circuit for providing a representation of pulmonary minute ventilation in a cardiac pacer which is implantable in a patient's body and which is operable in response to the value of pulmonary minute ventilation, said circuit comprising: a measurement and impedance/voltage conversion unit for detecting the impedance of a part of the patient's body where the impedance varies in dependence on respiration, said unit including sampling means which effects sampling of the impedance during discrete sampling times occurring at selected time intervals, and means for producing an output signal representative of the sampled impedance values; signal processing circuit means connected to said unit for producing, in response to the output signal from said unit, a signal representative of positive and negative deviations of the impedance from a selected base impedance value; and means for deriving from the signal representative of deviation a control signal for controlling the operation of the pacer; wherein said signal processing circuit means comprise:
- a first capacitor having a grounded plate and an ungrounded plate, and between which plates there is provided a first reference signal;
- a differential amplifier connected to receive said output signal from said unit and said first reference signal for producing a first comparison signal representative of the difference between said output signal and said first reference signal;
- a second capacitor having a grounded plate and an ungrounded plate;
- a first switch connected between said first differential amplifier and said ungrounded plate of said second capacitor for periodically supplying said first comparison signal to said second capacitor in time coincidence with the discrete sampling times associated with said sampling means, for periodically charging said second capacitor to establish at said ungrounded plate of said second capacitor a comparison signal voltage corresponding to said first comparison signal;
- a comparator having a first input connected to receive said comparison signal voltage, a second input connected to receive a constant reference voltage, and an output for providing a comparator output signal having a polarity representative of the polarity of said comparison signal voltage relative to said constant reference voltage;
- first and second signal controlled electronic devices each having an input, first and seond outputs and signal controllable means for conductively connecting said input to a selected one of said first and second outputs;
- means conductively connecting said ungrounded plate of said first capacitor to said first output of said first device and to said second output of said second device, and conductively connecting said ungrounded plate of said second capacitor to said second output of said first device and to said first output of said second device;
- first and second current sources supplying currents of respectively opposite polarities, each said current source supplying a sequence of constant amplitude current pulses at a constant rate which is higher than the rate of occurrence of the discrete sampling times associated with said sampling means;
- second and third switches each of which is connected between a respective one of said constant current sources and said input of a respective one of said electronic devices, and each of which is electronically controllable for selectively conductively connecting together said respective source and electronic device;
- logic circuit means having a main input, a start input, first and second outputs and means logically linking said outputs to said inputs, said main input of said logic circuit means being connected to said comparator output, said start input of said logic circuit means being connected to receive a periodic timing signal having the same period as, but offset in time from, the discrete sampling times associated with said sampling means, said first output of said logic circuit means being connected for electronically controlling said second and third switches, said second output of said logic circuit means being connected to said signal controllable means of said first and second electronic devices for supplying a control signal thereto, and said means logically linking said outputs to said inputs being operable for:
- supplying to said first output of said logic circuit means a signal for causing each of said second and third switches to selectively conductively connect together its said respective source and electronic device in response to each appearance of the periodic timing signal at said start input; and
- supplying to said second output of said logic circuit means a signal which is a function of the signals at said main and start inputs for controlling said devices in a manner to vary the charge on said second capacitor, after each occurrence of the periodic timing signal, to bring the value of the voltage at said ungrounded plate of said second capacitor to the value of the constant reference voltage, and to simultaneously vary the charge on said first capacitor in a manner to cause the voltage at said ungrounded plate of said first capacitor to change in a direction opposite to the direction of change of the voltage at said ungrounded plate of said second capacitor; whereby the voltage established at said ungrounded plate of said second capacitor during each discrete sampling time is proportional to the difference between the value of said output signal at that discrete sampling time and the value of said output signal at the immediately preceding discrete sampling time; and
- a fourth switch having an input connected to receive pulses of a clock signal at said constant rate which is higher than the rate of occurrence of the discrete sampling times associated with said sampling means, said fourth switch having an output and electronically controllable means operable for selectively conductively connecting its said input to its said output, said electronically controllable means of said fourth switch being connected to said first output of said logic circuit means for conductively connecting together said input and output of said fourth switch in response to each appearance of the periodic timing signal at said start input of said logic circuit means and for subsequently disconnecting said input and output of said fourth switch when the value of the voltage at said ungrounded plate of said second capacitor becomes substantially equal to the value of the constant reference voltage; and wherein
- said means for deriving a control signal comprise an electronic circuit connected to the output of said fourth switch for producing, as the control signal, a signal having a value whih varies as a function of the average value of the successive voltage values established at said ungrounded plate of said second capacitor, which average value is proportional to pulmonary minute ventilation.

* * * * *